United States Patent
Balfour et al.

(10) Patent No.: US 7,341,454 B2
(45) Date of Patent: Mar. 11, 2008

(54) ATTACHMENT MECHANISM FOR DENTAL IMPLANTS

(75) Inventors: Alan R. Balfour, Petaluma, CA (US); Bradly S. McAllister, Tigard, OR (US); Joseph Edward Carchidi, West Bridgewater, MA (US)

(73) Assignee: ACE Surgical Supply Co, Inc., Brockton, MA (US)

( * ) Notice: Subject to any disclaimer, the term of this patent is extended or adjusted under 35 U.S.C. 154(b) by 0 days.

(21) Appl. No.: 11/122,696

(22) Filed: May 5, 2005

(65) Prior Publication Data

US 2005/0208453 A1 Sep. 22, 2005

Related U.S. Application Data

(63) Continuation of application No. 10/265,522, filed on Oct. 3, 2002, now abandoned.

(60) Provisional application No. 60/326,707, filed on Oct. 4, 2001.

(51) Int. Cl.
*A61C 8/00* (2006.01)

(52) U.S. Cl. .................................. 433/173; 433/174
(58) Field of Classification Search ........ 433/173–176, 433/201.1
See application file for complete search history.

(56) References Cited

U.S. PATENT DOCUMENTS

| | | | |
|---|---|---|---|
| 4,960,381 A | 10/1990 | Niznick | |
| 6,174,167 B1 | 1/2001 | Wohrle | |
| 6,217,333 B1 | 4/2001 | Ercoli | |
| 6,280,195 B1* | 8/2001 | Broberg et al. | 433/201.1 |
| 6,358,050 B1* | 3/2002 | Bergstrom et al. | 433/173 |
| 2001/0000748 A1* | 5/2001 | Rogers et al. | 433/172 |

* cited by examiner

*Primary Examiner*—Cris Rodriguez
*Assistant Examiner*—Candice C Stokes
(74) *Attorney, Agent, or Firm*—John A Haug

(57) ABSTRACT

An endosseous dental implant system has an externally threaded root-formed base 2 with self-tapping flutes 5 formed into apical threads of the root-formed base for easy insertion and immediate locking in an osteotomy. The coronal portion of the base has either a male or a female self-locking tapered friction held post that includes an apical anti-rotational polygon 7, 23 to lock a prosthetic attachment to the base once attached.

2 Claims, 4 Drawing Sheets

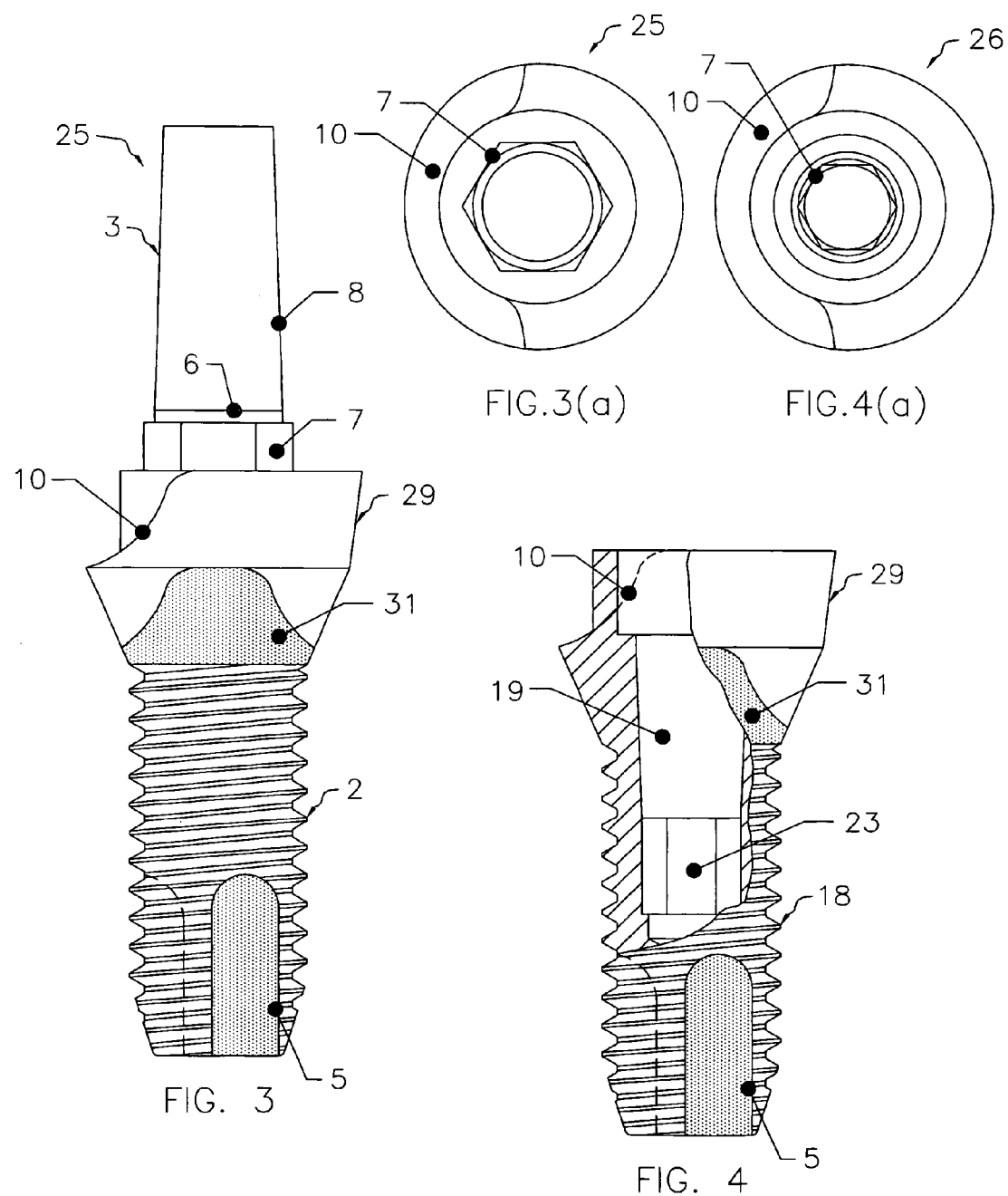

ATTACHMENT MECHANISM FOR DENTAL IMPLANTS

CROSS REFERENCE TO RELATED APPLICATIONS

This is a Continuation of U.S. application Ser. No. 10/265,522, filed Oct. 3, 2002 now abandoned. Priority is claimed under 35 U.S.C. Section 119(e)(1) of Provisional Application No. 60/326,707, filed Oct. 4, 2001.

FIELD OF THE INVENTION

This invention relates generally to artificial orthopedic implant prosthesis and more particularly, but not limited to, dental implants.

BACKGROUND OF THE INVENTION

Over the last several decades many root-formed dental implants have been designed to replace natural dentition and provide for both esthetic and functional occlusion. Although these designs provide for the functional replacement of natural dentition that was either lost or missing, creating the natural inter-proximal tissue between adjacent implants has remained esthetically a restorative challenge. In fact, to maintain the soft tissue papilla between adjacent implants requires that the underlying inter-proximal bone area be two to three millimeters higher than in the buccal and lingual areas. Since most dental implants are not placed in a fresh tooth extraction site, where this physiological inter-proximal profile naturally occurs, grafting or countersinking the implant may be required to obtain this inter-proximal bone between the implants. Once the desired bone profile around the implant is surgically achieved, maintaining this inter-proximal bone for natural esthetics has remained a physiological challenge.

SUMMARY OF THE INVENTION

It is an object of the present invention to overcome the limitations of the prior art noted above. Another object of the invention is to provide a root-formed dental implant which emulates the anatomical characteristics of natural dentition that can be easily manufactured and surgically placed. Another object of the invention is to provide such an implant with an anti-rotational interlocking mechanism to drive and secure the implant into the jaw and act as a receptor for securing a prosthetic attachment. A further object of the invention is the provision of a single or multiple unit implant that incorporates a defined inter-dental geometry to preserve and control inter-proximal bone and papilla.

Briefly, according to a preferred embodiment of the invention, a dental implant comprises an elongated externally threaded base for receipt in an osteotomy, the base having a head portion integrally formed therewith and from which an integrally formed male or female prosthetic attachment mechanism extends, the prosthetic attachment mechanism having a generally cylindrical smooth attachment surface formed with a self locking taper and an anti-rotational polygonal surface portion in series with the attachment surface.

BRIEF DESCRIPTION OF THE DRAWINGS

Other objects, advantages and details of the invention appear in the following detailed description of the preferred embodiment, the detailed description referring to the drawings in which like reference characters refer to like components or structural features.

FIG. 3 is an elevational view of a modification of the FIG. 1 single stage endosseous dental implant having a scalloped out buccal recessed portion and FIG. 3(a) is a top view thereof;

FIG. 4 is an elevational view, partly in cross section, of a modification of the FIG. 3 two stage endosseous dental implant having a scalloped out buccal recessed portion and FIG. 4(a) is a top view thereof;

DETAILED DESCRIPTION OF PREFERRED EMBODIMENTS

Figure 1:
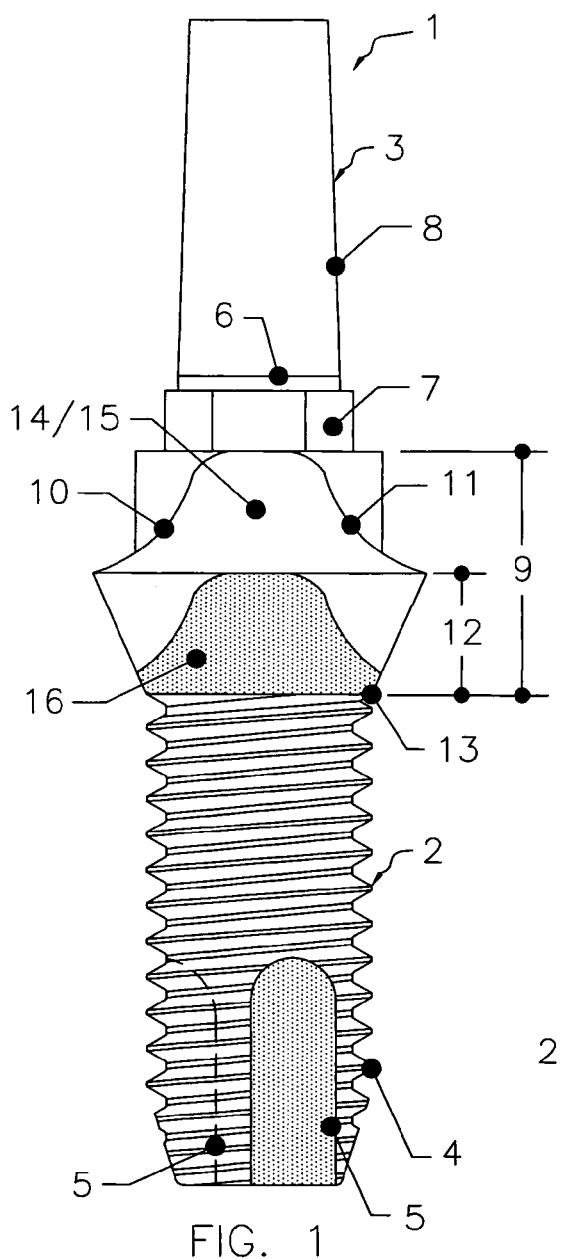
FIG. 1 is an elevational view of a single stage endosseous dental implant with scalloped out buccal and lingual recessed portions made in accordance with a preferred embodiment of the invention and FIG. 1(a) is a bottom view of the end face of the base of the FIG. 1 implant.
Figures 1A, 2A:
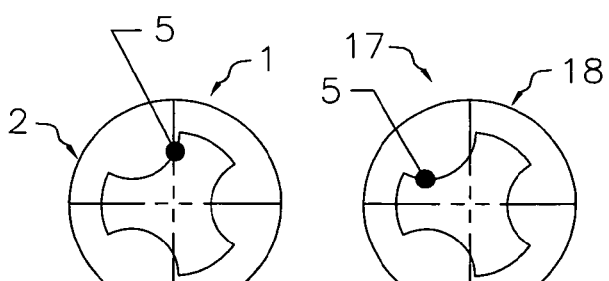

With reference to FIGS. 1 and 1(a), a single stage endosseous dental implant 1 made according to a first preferred embodiment of the invention comprises a root-formed externally threaded base 2 and a tapered interlocking coronal prosthetic attachment post 3. Incorporated at the apex of the root-formed externally threaded base is a self-tapping thread 4 which will pull the implant downwardly during its initial placement. To assist in this process and to lock the implant into place, thread 4 utilizes specially designed cutting flutes 5 to cut, form and lock the implant into place. At the foot 6 of the tapered interlocking coronal prosthetic attachment post 3 is an anti-rotational polygonal surface 7 to lock the prosthetic attachment to root-formed implant 1, once it is attached. To assure that the prosthesis remains attached to root-formed implant 1, the male tapered post 3 uses a defined self-locking taper angle 8, shown extending from demarcation line 6, that friction locks with a female mate having a complimentary self-locking taper. Once the prosthesis is permanently attached to the tapered post, the now single unit implant and prosthesis is secured and cannot be rotated or removed.

An esthetic coronal profile head 9 is disposed between root-formed externally threaded base 2 and tapered interlocking coronal prosthetic attachment post 3. A unique scalloped out profile 10, 11 is formed in head 9 to replicate the buccal and lingual areas of a natural tooth. These scalloped out areas comprise generally smoothly curved recesses in an annular margin of a selected thickness machined within a one to two millimeter distance 12 to the beginning of the implant's first thread 13. This one to two millimeter separation 12 allows for the clinically accepted bone resorption between the implant and prosthesis connection to end at the first thread 13 of the implant. Ninety degrees to scalloped out profiles 10, 11 are enhanced profile areas for the inter-proximal zones 14, 15, which are also designed to replicate the bone in between natural dentition. These areas preferably are further textured at 16, by forming micro indentations or the like on the order of 30-50 microns, as by blasting with appropriate particulate material known in the art, to enhance bone attachment to the implant in these areas. Even with the standard one to two millimeter bone resorption in these areas 14, 15, the additional textured surface 16 assures preservation and control of the inter-dental bone and papilla for the desired esthetics. The scalloped out recesses replicate the inter-dental geometry of a natural tooth and assist in the maintenance of the alveolar housing and gingival soft tissue.

Figure 2:
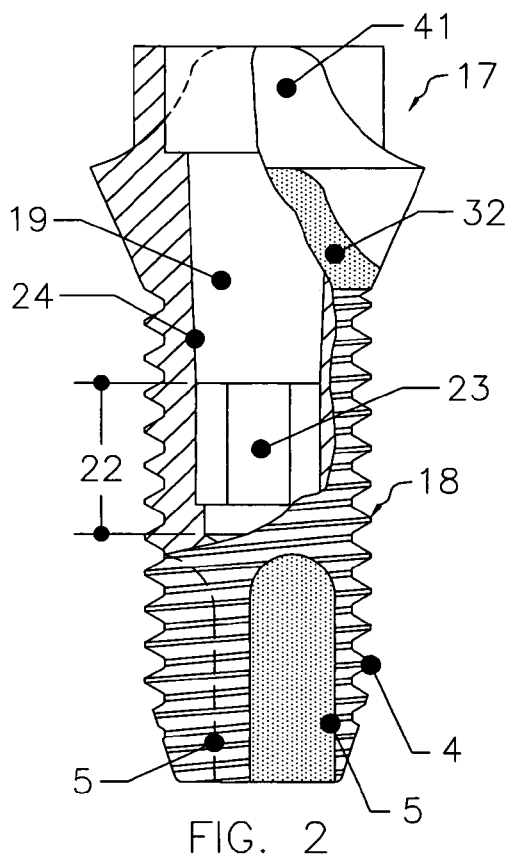
FIG. 2 is an elevational view of a two stage endosseous dental implant with scalloped out buccal and lingual recessed portions made in accordance with a second preferred embodiment of the invention and FIG. 2(a) is a bottom view of the base of the FIG. 2 implant.

FIGS. 2 and 2(*a*) show the endosseous dental implant 17 made in accordance with a second preferred embodiment of the invention for use with a two stage surgical process. Implant 17 comprises a root-formed externally threaded base 18 with an internally tapered, interlocking prosthetic attachment plug receiving bore 19. As described with reference to FIG. 1, the apex of the root-formed externally threaded base 18 is a self-tapping thread 4 which pulls the implant downward during its initial placement. To assist in insertion and to lock the implant in place, threaded base 18 utilizes specially designed cutting flutes 5 to cut, form and lock the implant into place. An anti-rotational polygonal surface 23 is positioned at the apex 22 of the tapered prosthetic attachment plug receiving bore 19 of the implant to lock the prosthetic attachment to implant 17 once it is attached. To assure that the prosthesis remains attached to the root-formed implant the female tapered plug receiving bore 19 uses a defined self-locking taper angle 24 that friction locks with the plug of a male prosthetic mate such as post 42 of FIG. 6(*a*) having a complimentary self-locking taper, to be discussed. Once the prosthesis is permanently attached in the tapered plug receiving bore 19 the now formed single unit implant and prosthesis is secured and cannot be rotated or removed without the assistance of a specially designed removal tool, to be discussed.

FIGS. 3 and 4, respectively, show the single and two stage esthetic implant embodiments 25,26 modified to include only a single scalloped cut-out 10 formed on the buccal faces of the implants. In these embodiments, the lingual profile 29 is at the same height or level as the inter-proximal sides of the implants. Also lingual side surface texturing 31 extends above the threads to assist in tissue attachment on this side. Since the lingual side 29 has no esthetic concerns, keeping the material in this area of the implant improves structural characteristics of the implant and simplifies the laboratory restorative challenges. In all the implant designs, 1,17,25,26, alignment of the anti-rotational polygonal prosthetic attachment 7,23 with the scalloped out profile 10 on the buccal side of the implant 1,25,26, assist for correct placement of the implant in its desired rotational location.

Figures 5, 5A:
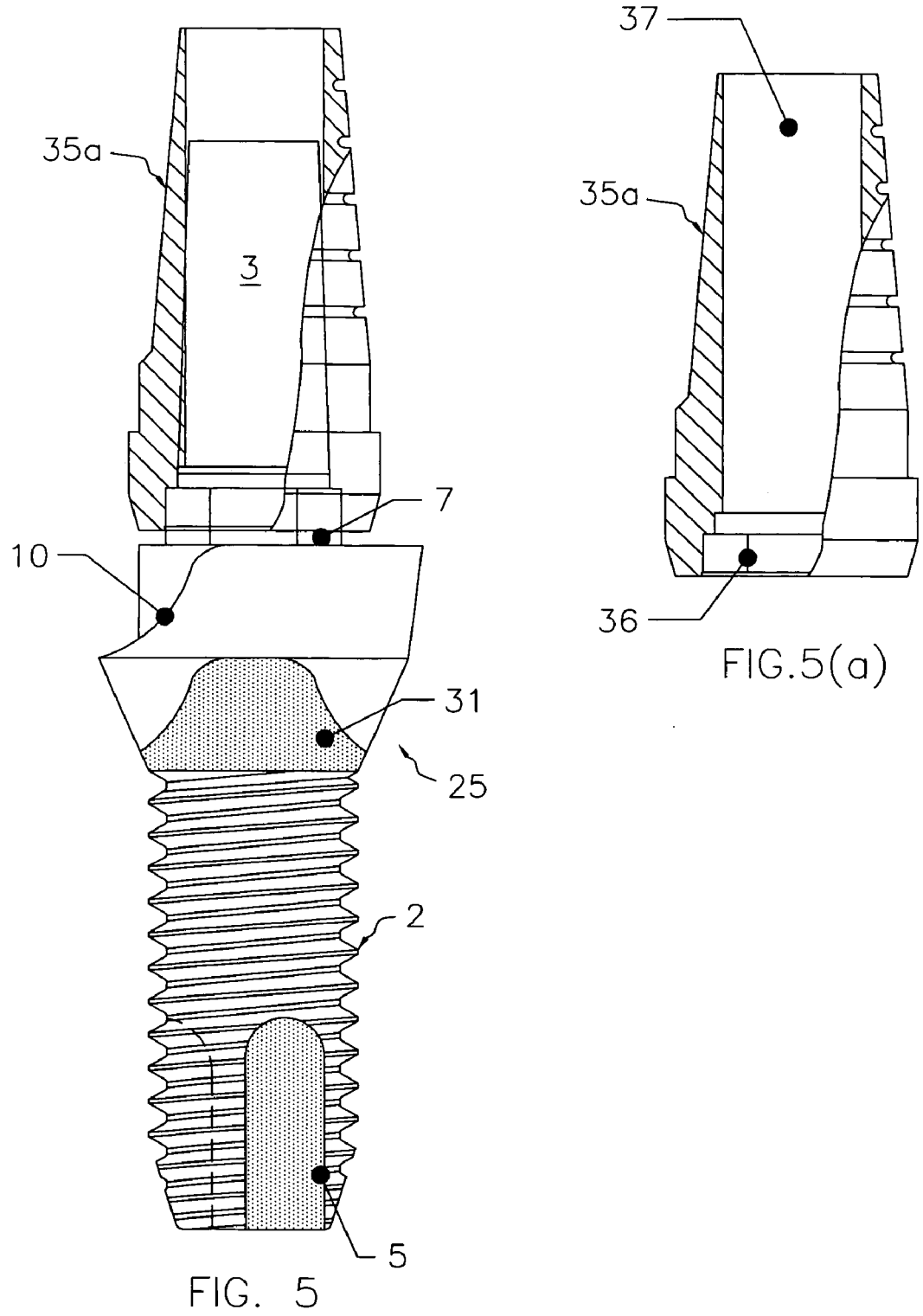
FIG. 5 is an elevational view of a single stage endosseous dental implant as shown in FIG. 3 with an assembled and attached prosthetic abutment shown separately in FIG. 5(a)
Figure 6:
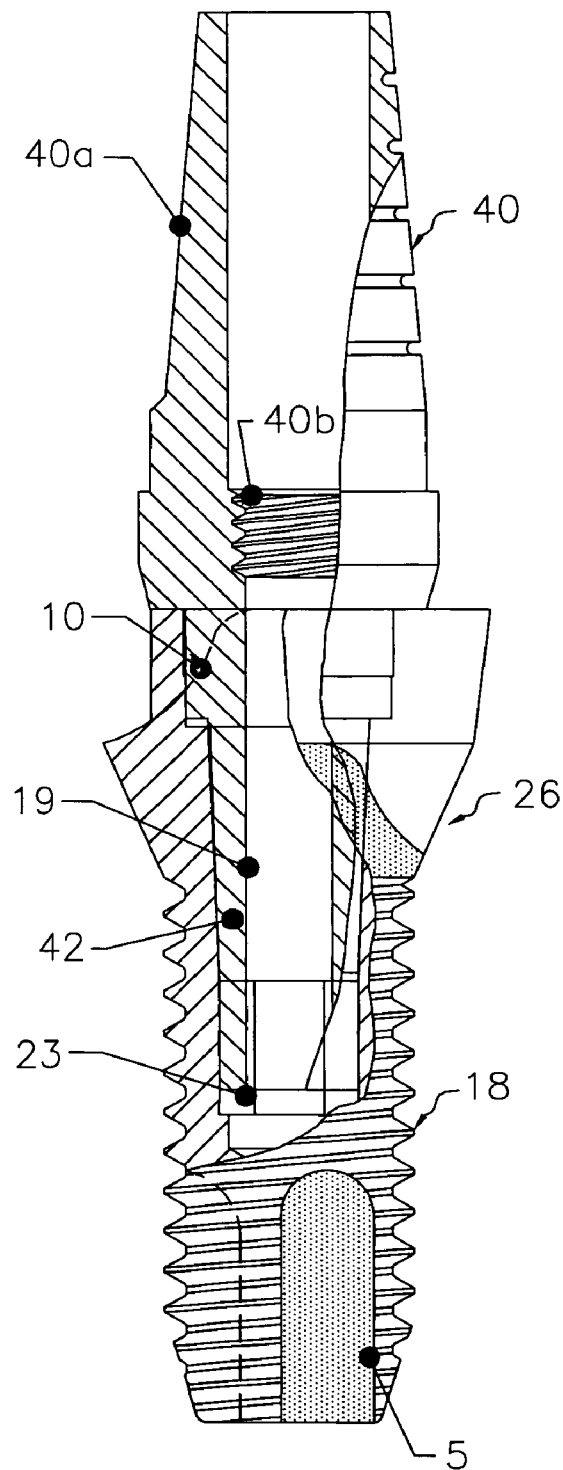
FIG. 6 is an elevational view of a two stage endosseous dental implant as shown in FIG. 4 with an assembled and attached prosthetic abutment shown separately in FIG. 6(a).
Figure 6A:
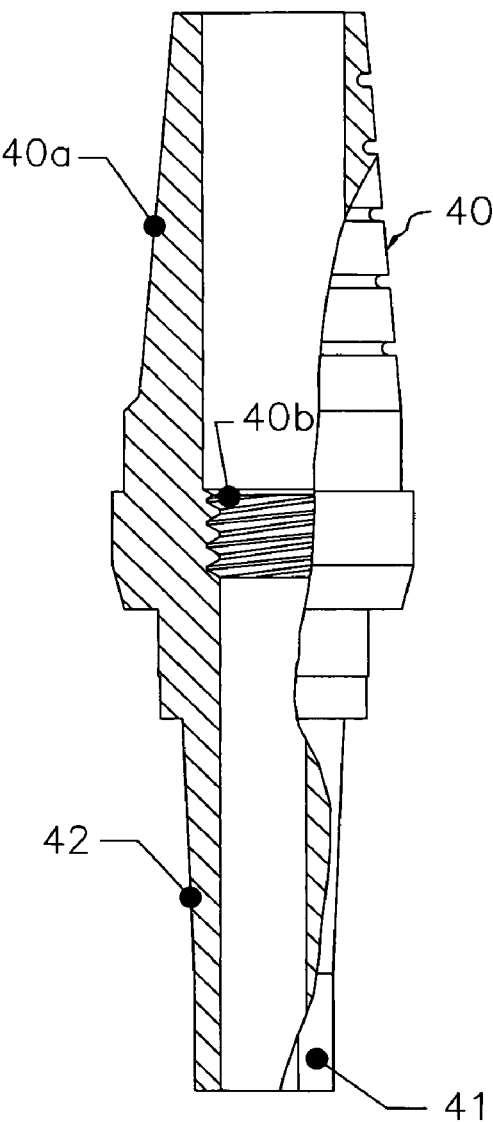

FIGS. 5 and 6 show how the restorative attachments are made for either the single or the two-stage esthetic implant embodiments. The restorative prosthetic attachment 35, shown in FIG. 5(*a*) with an exemplary outer surface configuration having a generally tapered, grooved cylinder formed with a flat 35*a*, is used with the single stage implant embodiment. Prosthetic attachment 35 includes a female polygonal surface 36 and self-locking tapered plug receiving bore 37 that engages the male polygonal surface 7 and friction locks on the male plug or post 3 of the implant. With reference to FIG. 6, restorative prosthetic attachment 40, with an exemplary outer surface configuration including flat 40*a*, is used with the two stage implant embodiment. Prosthetic attachment 40 comprises a male polygonal portion 41 and tapered plug or post 42 that engages the female polygonal surface 23 and friction locks on the female post receiving bore 19 of the implant. In both cases1 once the prosthetic attachment is locked onto the implant, the restoration becomes one unit and cannot be rotated. However, in the FIG. 6 embodiment, prosthetic attachment 40 is provided with internal threads 40*b* which allow for the use of a specially designed jack screw removal tool to apply sufficient force for removal, if desired.

Although the invention has been described with regard to specific preferred embodiments thereof, many variations and modifications will become apparent to those skilled in the art. It is, therefore, the intent that the appended claims be interpreted as broadly as possible in view of the prior art to include all such variations and modifications.

What is claimed:

1. A dental implant comprising an elongated base having opposed first and second end portions for receipt in an osteotomy, the base having an integrally formed head portion extending from the second end portion of the base and having a coronal surface, and a thread-less prosthetic attachment mechanism integrally formed on the head portion for receiving and attaching thereto a selected prosthesis, the prosthetic attachment mechanism including a plug receiving bore formed in the base through the coronal surface, the bore having a generally cylindrical, smooth attachment surface with a self-locking taper in series with a female anti-rotational polygonal surface disposed on the first end portion side of the cylindrical smooth, attachment surface, further comprising a prosthetic attachment having a generally cylindrical plug having an outer surface formed with a self-locking taper complimentary to the plug receiving bore, the plug having a first end portion beyond the taper formed as a polygonal surface complimentary to the female polygonal surface in the plug receiving bore and a prosthetic receiving post extending coronally from the cylindrical plug, at least a portion of the prosthetic attachment being tubular formed with an internal threaded portion to allow for threaded engagement with a screw removal tool to enable removal of the prosthetic attachment.

2. A dental implant comprising a base having first and second opposed portions for receipt in an osteotomy having an open and a closed end, the first opposed portion of the base adapted to be disposed in the osteotomy facing the closed end, a head portion integrally formed with the base at the second opposed portion of the base, the head portion having a coronal surface, a thread-less prosthetic attachment mechanism integrally formed on the head portion at the second portion of the base for receiving and attaching a selected prosthesis, the prosthetic attachment mechanism having a plug receiving bore formed in the base through the coronal surface to an apical end, the bore having a first generally cylindrical, smooth attachment surface formed with a self-locking taper for securing the prosthesis having a complimentary generally cylindrical surface formed with a matching self-locking taper, the prosthetic attachment mechanism having a second anti-rotational polygonal surface in series with the first attachment surface and disposed on the side of the first attachment surface closest to the first opposed portion of the base for preventing rotational movement of a prothesis having a complimentary anti-rotational surface, the second anti-rotational polygonal surface being a female polygonal surface formed in the plug receiving bore on the apical side of the first attachment surface.

* * * * *